United States Patent [19]

Pirotzky et al.

[11] Patent Number: 5,892,023

[45] Date of Patent: Apr. 6, 1999

[54] ANTI SENSE OLIGONUCLEOTIDES FOR BLOCKING IGE RECEPTOR SYNTHESIS

[75] Inventors: Eduardo Pirotzky, Paris; Soudhir Colote, Les Ulis, both of France

[73] Assignee: Societe de Conseils de Recherches et D'Applications Scientifiques (S.C.R.A.S.), France

[21] Appl. No.: 952,597

[22] PCT Filed: May 24, 1996

[86] PCT No.: PCT/FR96/00785

§ 371 Date: Nov. 20, 1997

§ 102(e) Date: Nov. 20, 1997

[87] PCT Pub. No.: WO96/37605

PCT Pub. Date: Nov. 28, 1996

[30] Foreign Application Priority Data

May 26, 1995 [GB] United Kingdom ............... 9510718

[51] Int. Cl.⁶ .......................... C07H 21/04; A61K 48/00
[52] U.S. Cl. ................ 536/24.5; 536/24.1; 536/24.3; 536/24.31; 536/24.33; 435/6; 514/44
[58] Field of Search ............... 435/6, 172.3, 375, 435/377; 536/24.1, 24.5; 514/44

[56] References Cited

FOREIGN PATENT DOCUMENTS 9321317  10/1993  WIPO .
9509002   4/1995  WIPO .

OTHER PUBLICATIONS

Uhlman et al. "Antisense Oligonucleotides: A New Therapeutic Principle." Chemical Reviews vol. 90 No. 4:544–584, Jun. 1990.

Agrawal, S., "Antisense Oligonucleotides: Towards Clinical Trials" Tibtech vol. 14 376–387, 1996.

Branch, A. "A Good Antisense Molecule is Hard to Find". Tibs vol. 23:45–50, Feb. 1998.

Fournier et al, "Role . . . Proliferation", Blood, vol. 84, No. 6 (1994) pp. 1881–1886.

Zon, "Oligonucleotide . . . Agents", Pharmaceutical Research, vol. 5, No. 9 (1988) pp. 539–549.

Bhatti et al, "Inhibition . . . Epsilon R II", Cell Immunol. 144 (1) (1992) pp. 117–130.

Liu et al, "CDNA . . . Receptor", Proceedings of the National Academy of Sciences of USA, vol. 85, No. 15, pp. 5639–5643.

*Primary Examiner*—George C. Elliott
*Assistant Examiner*—Sean McGarry
*Attorney, Agent, or Firm*—Bierman, Muserlian and Lucas

[57] ABSTRACT

The invention is drawn to antisense oligonucleotides directed to the inhibition of the IgE receptor synthesis.

12 Claims, No Drawings

ANTI SENSE OLIGONUCLEOTIDES FOR BLOCKING IGE RECEPTOR SYNTHESIS

The present invention concerns antisense oligonucleotides which selectively hybridize with one or more genes necessary in blocking the synthesis of the IgE receptor, pharmaceutical compounds comprising them, and their use as IgE inhibitors.

The hypersensitivity of IgE is at least one of the major components exerting a mediating effect in the manifestation of the early and late phases of type I allergic reactions. The physiopathological mechanism may be broken down into the following phases:

abnormal production of large quantities of IgE;

secretion of spasmogenic and vasoactive mediators;

induction of an inflammatory response rich in eosinophils.

Mastocytes and basophils are not the only target cells activated by IgE and intervening in the hypersensitivity reaction. The other effector cells are comprised of epithelial and endothelial cells and other inflammatory cells.

The hypersensitivity reaction is triggered when IgE, produced in excess by B lymphocytes, enters into interaction with the specific receptors on the effector cells.

Two types of receptors have been characterized: one high affinity receptor called the $Fc_\epsilon R_I$ receptor, or type I receptor, and a weak affinity receptor called the $Fc_\epsilon R_{II}$ receptor, or type II receptor. In addition to the cells intervening in the inflammatory response, these receptors are expressed equally by the sub-population in B and T lymphocytes. The expression of type I receptors or $Fc_\epsilon R_I$ is necessary to unleash the hypersensitivity reaction.

One therapeutic approach to the treatment of allergic reactions consists of blocking the synthesis of IgE or the IgE receptors.

The antisense strategy is a new therapeutic approach intended to obtain the selective modulation of gene expression by an highly selective association with a nucleotide chain (oligonucleotide) with its supplementary sequence on the RNA or DNA messengers or pre-messengers and, consequently, inhibiting the synthesis of the corresponding proteins.

Oligonucleotides complementary to the transcriptional products arc called "antisense" oligonucleotides. The oligonucleotides having the same sequence as the transcriptional products are named "sense" oligonucleotides. Initially these compounds were logically destined to inhibit the formation of a gene product by the suppression of the corresponding RNA messenger, via the mechanism of hydrolytic catilization by the RNAase H. It soon became apparent that the action mechanism of these antisense oligonucleotides was not this simple. These oligonucleotides can interact with a certain number of target cells not containing nucleic acid. These oligonucleotides can interact with the gene, to form triple-helices structures and can inhibit the formation of transcriptional products. Oligonucleotides can interact with the intron-exon junctions of the RNA pre-messenger, thus interfering with the correct splicing of the transcriptional product. Oligonucleotides can hybridize with the messenger RNA in the cytoplasm, by forming an RNA-DNA complex, which is rapidly digested by the enzyme RNAase H, or by preventing the ribosome complex from sliding along the messenger RNA hence blocking its transduction.

Oligonucleotides and, more particularly, modified oligonucleotides, can interact with a number of cellular products such as proteins. These interactions may be sequence specific (for example: transcription factors) or non-sequence specific (for example: growth factors).

Oligonucleotides are often used as a probe, for example for the identification of a complementary strand of the studied oligonucleotide, from an experimental point of view, in pharmacological experiments. For instance, in the domain of IgE, oligonucleotides were used, for example, to prominently display the subunit of the IgE receptor (Proceedings of the National Academy of Sciences of USA, Vol. 85, No. 15, August 1988, pp. 5639–5643). But in this domain, none of the oligonucleotides were used for therapeutic purposes.

The invention concerns the antisense oligonucleotides that selectively hybridize with one or more of the genes necessary to block the synthesis of the IgE receptor.

This invention concerns more particularly the antisense oligonucleotides that selectively hybridize with a gene or transcriptional products for the α subunits of the high affinity IgE receptor. These oligonucleotides preferably comprise [anywhere] from 8 to 35 units. Even more preferable are oligonucleotides comprising from 10 to 25 units.

The term "oligonucleotide" represents an oligonucleotide made up of bases, phosphodiester bonds and sugars well known by persons skilled in the art. The term oligonucleotide represents as well oligonucleotides in which the skeleton has been modified either on the entire length of the oligonucleotide or in the 5' position and/or in the 3' position. In effect, oligonucleotides are sensitive to certain enzymes, nucleases which split them into nucleotides; oligonucleotides become resistant to nucleases by modifications, for example, from the chemical nature of sugar itself or the sugar-phosphate chain: in this manner the phosphodiester chain may be replace, for example, by a phosphorothioate, phosphorodithioate, methylphosphonate, phosphoramidate, phosphoethlytriester, butylamidate, piperazidate or morpholidate chains. Other types of modifications may be made along the entire length of the oligonucleotide or to its 5' and/or 3' extremities, to render the oligonucleotides more resistant to a biological environment. Phosphate bonds between the nucleotides may also be replace by amide bonds (peptidic nucleic acids). Moreover, the transmembranous passage of the oligonucleotide may be favored by rendering the latter more hydrophobic; this may be obtained, for example, by attaching hydrophobic substituents such as cholesterol or aromatic groups or a polymer. The modified bases may be partially incorporated or along the entire length of the oligonucleotide. Conformationally modified nucleotides resistant to nucleases or with improved properties of intracellular absorption or of hybridization may be incorporated partially or along the entire length of the nucleotide. Thus the expression "oligonucleotide" represents as well a nucleotide whose skeleton is modified according to any one of the methods described above or of any other methods known well by a person skilled in the art.

More particularly, the invention has in mind oligonucleotides of sequences: SEQ ID No. 1 to SEQ ID No. 6 respectively; oligonucleotides with the sequence SEQ ID No. 4–6 are the oligonucleotides in which all of the phosphodiester bonds were modified into phosphorothioate. Their complimentary sequences, or the sense oligonucleotides according to the invention, may also be used.

The invention concerns as well, antisense oligonucleotides comprised of at least one fragment of one of the selected sequences among the SEQ ID No. 1 to SEQ ID No. 6 sequences.

The oligonucleotides of the invention may be synthesized by any one of the known methods of chemical synthesis of oligonucleotides. Antisense oligonucleotides are very advantageously prepared by using any automatic synthesizer of commercial nucleic acids. One of these methods of synthesis of the oligonucleotides is the beta-cyanoethyl phosphoramidate method described by S. L. Beaucage et al.(Tet. Let. 22(1981), 1859–1862).

The invention has in mind pharmaceutical compositions as well containing, as an active ingredient, at least one of the antisense oligonucleotides according to the invention, mixed with an excipient and/or pharmaceutically acceptable medium, according to the chosen method of administration. The mixture may be administered by means of a topical, systemic or local treatment. It can take the form of a liquid for an injection, a time released formula liposome, or the form of a gel, an ointment for a local application or any other acceptable form according to the chosen method of administration. Preferably, the mixture is used in the form of a liposome.

Finally, the invention concerns the use of oligonucleotides according to the invention, for the preparation of medicines used to inhibit the role of IgE. The invention concerns more particularly the use of oligonucleotides according to the invention, for the preparation of medicines used for the treatment of allergies or other pathologies in which the IgE receptor is implicated.

The inhibiting role of the oligonucleotides is determined in the study below.

The cell lines RBL 2H3 (modified mastocytes of rat) were cultivated in a RPMI-1640 medium, in the presence of a 10% fetal calf serum (FCS). These cells were cultured with a ratio of $5 \times 10^4$/mL on day 0, with or without the oligonucleotides according to the invention, with a concentration of 1 or $10 \times 10^{-6}$M, in solution or in the form of a liposome. On day 2, the culture medium was reconstituted and the oligonucleotides were added in the same concentration and in the same form. The cells were again cultured for 2 days and isolated on day 4, immunomarked by using an antibody of the anti-subunit α of the high affinity IgE receptor of rats, and analyzed by FACS.

The RBL 2H3 cells, cultured under different conditions, were isolated by tripsination and counted. For each condition, two sample aliquots of $5 \times 10^5$ cells were treated with PBS/2% fetal calf serum. One of the two sample aliquots was treated with an antibody of the anti-subunit α of mouse (antibody BC4) then with an anti-Ig of mouse, marked with fluresceine isothiocyanate (FITC); the other sample aliquot was treated only with the secondary antibody (anti-Ig FITC) and was used as a negative witness. The percentage of fluorescent cells, in each case, was determined by cytofluorimetric analysis.

The results are summarized in the table below:

| | Formulation | Pro-por-tion $\mu$M | % of spontaneous fluorescence (Anti-Ig FITC) | % of Fluorescence after marking with the antibody of the anti-subunit α (BC4) |
|---|---|---|---|---|
| Control | | | 1.0 | 98.4 |
| SEQ ID No. 4 | Solution | 1 | 0.9 | 98 |
| SEQ ID No. 5 | Solution | 1 | 0.9 | 97.6 |
| SEQ ID No. 6 | Solution | 1 | 0.9 | 98.1 |
| SEQ ID No. 4 | Solution | 10 | 0.7 | 98.2 |
| SEQ ID No. 5 | Solution | 10 | 0.8 | 98.1 |
| SEQ ID No. 6 | Solution | 10 | 0.8 | 98.1 |
| SEQ ID No. 4 | Liposome | 1 | 0.1 | 82.8 |
| SEQ ID No. 5 | Liposome | 1 | 0.1 | 4.5 |
| SEQ ID No. 6 | Liposome | 1 | 1.0 | 99.0 |

We claim:

1. An oligonucleotide comprising 10 to 25 nucleotide units and which selectively hybridizes with at least one gene necessary to block the synthesis of the IgE receptor and comprises a sequence selected from the group consisting of SEQ ID Nos: 1 to 6.

2. An oligonucleotide as claimed in claim 1, that selectively hybridizes with genes or transcriptional products for the α subunits of the high affinity IgE receptor.

3. An oligonucleotide as claimed in claim 1, which consists of a sequence selected from group consisting of SEQ ID No: 1 to SEQ ID No: 6.

4. An oligonucleotide as claimed in claim 1, in which the phosphate backbone is modified.

5. An oligonucleotide as claimed in claim 4, in which the nucleotidic base is modified.

6. An oligonucleotide as claimed in claim 5, in which a modified nucleotidic base presents the α anomer conformation.

7. An oligonucleotide as claimed in claim 4, in which at least one of the phosphate bond groups is modified.

8. An oligonucleotide as claimed in claim 7, in which at least one of the phosphate bond groups is modified into phosphorothioate.

9. An oligonucleotide as claimed in claim 8, which consists of a sequence selected from the group consisting of SEQ ID No: 1 to SEQ ID No: 6.

10. An oligonucleotide as claimed in claim 4, in which either the 5' position or the 3' position or the 5' and 3' positions is modified.

11. An oligonucleotide as claimed in claim 10, in which either the 5' position or the 3' position or the 5' and 3' positions is modified by the substitution of a hydrophobic group.

12. An oligonucleotide as claimed in claim 10, in which either the 5' position or the 3' position or the 5' and 3' positions is modified by the substitution of a protector group.

* * * * *

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO: 1:

TAGATCACCT TGT                                                                                              1 3

( 2 ) INFORMATION FOR SEQ ID NO: 2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO: 2:

TAATGGAGAT GTTGT                                                                                            1 5

( 2 ) INFORMATION FOR SEQ ID NO: 3:

```
        ( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( i v ) ANTI-SENSE: YES ( x i ) SEQUENCE DESCRIPTION: SEQ ID NO: 3:

GCAAACAGAA TCACC                                                                        15

( 2 ) INFORMATION FOR SEQ ID NO: 4:

( i ) SEQUENCE CHARACTERISTICS:
                ( A ) LENGTH: 13 base pairs
                ( B ) TYPE: nucleic acid
                ( C ) STRANDEDNESS: single
                ( D ) TOPOLOGY: linear ( i v ) ANTI-SENSE: YES ( x i ) SEQUENCE DESCRIPTION: SEQ ID NO: 4:

TAGATCACCT TGT                                                                          13

( 2 ) INFORMATION FOR SEQ ID NO: 5:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( i v ) ANTI-SENSE: YES ( x i ) SEQUENCE DESCRIPTION: SEQ ID NO: 5:

TAATGGAGAT GTTGT                                                                        15

( 2 ) INFORMATION FOR SEQ ID NO: 6:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( i v ) ANTI-SENSE: YES ( x i ) SEQUENCE DESCRIPTION: SEQ ID NO: 6:

GCAAACAGAA TCACC                                                                        15
```